United States Patent [19]

Clayton

[11] 4,297,997
[45] Nov. 3, 1981

[54] METHOD AND DEVICE FOR RETAINING COLON CLEANSING TUBE IN PLACE

[76] Inventor: Ralph S. Clayton, Hendrick Professional Center, 1100 N. 19th St., Abilene, Tex. 79601

[21] Appl. No.: 150,424

[22] Filed: May 16, 1980

Related U.S. Application Data

[63] Continuation-in-part of Ser. No. 937,591, Aug. 28, 1978.

[51] Int. Cl.³ ............................................. A61F 13/00
[52] U.S. Cl. .................................................. 128/169
[58] Field of Search ............... 128/246, 169, 133, 134, 128/DIG. 15, 78, 95, 96, 157, 1 R

[56] References Cited

U.S. PATENT DOCUMENTS 1,995,002  3/1935  Lee ........................................ 128/78
3,298,366  1/1967  Moore et al. .................... 128/169 X Primary Examiner—John D. Yasko
Attorney, Agent, or Firm—Larson and Taylor

[57] ABSTRACT

A method and apparatus for keeping a tube in place within a person's anal opening, such as for administering a cleansing liquid or the like. A band device is wrapped around the person's mid-section and strap ends which overlap each other in the vicinity of the person's buttocks are pulled tight and secured. The strap attachments are preferably Velcro. The central section of the band includes a quick release connection permitting removal of the band without disconnecting the straps. Prior to attaching the band, it may be preferable to wrap around the tube up against the anal opening a thick cord of an absorbent material.

18 Claims, 8 Drawing Figures

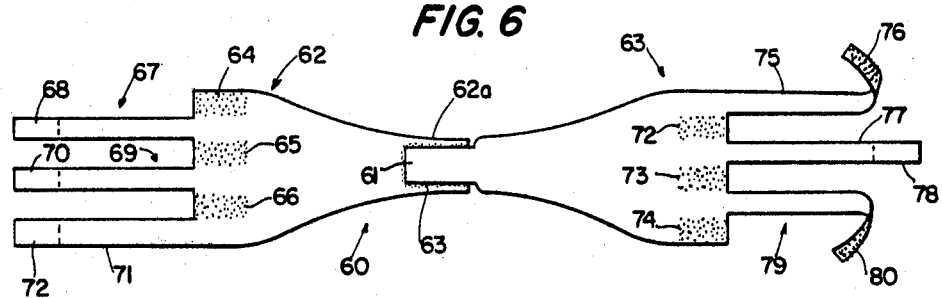
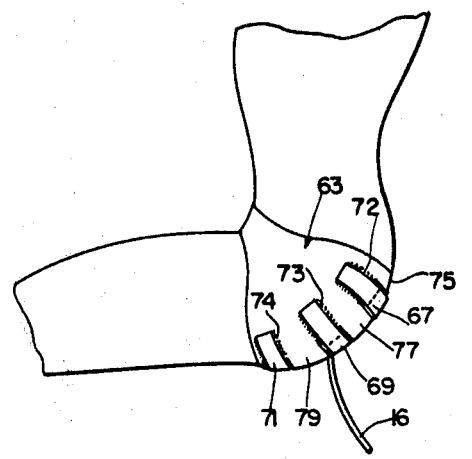
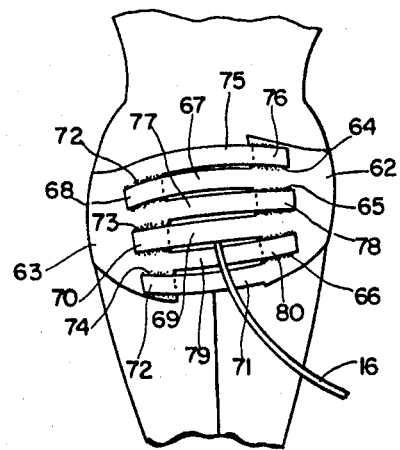

METHOD AND DEVICE FOR RETAINING COLON CLEANSING TUBE IN PLACE

RELATED APPLICATION

This application is a continuation-in-part of my prior, co-pending Application Ser. No. 937,591, filed Aug. 28, 1978.

BACKGROUND OF THE INVENTION

This invention relates to the introduction of liquid into a person's colon through the anal opening, and in particular it relates to a new and improved method and device for retaining a tube in place in the person's anal opening while administering the cleansing or other liquid.

My prior application which is referred to above relates to a new and improved method and technique for cleansing the colon. Included as a part of that method and technique is the introduction into a person's colon of a tube for administering a cleansing liquid, said tube having a balloon near the end thereof adapted to be inflated within the patient's anal opening to hold the tube in place. In any procedure wherein such a tube must remain in place within the person's anal opening, but particularly in the methods and techniques described in my earlier application wherein large quantities of liquid are introduced and held therein for a significant period of time, there is a tendency for the patient to expel the tube and hence a need exists for a means for preventing such expulsion.

While it is of course the purpose of the balloon to prevent such expulsion of the tube, there are many situations wherein the balloon cannot in and of itself prevent such expulsion.

Another problem which occurs when using such balloons is that they are subjected to asymmetrical and significant forces tending to tilt the balloon and otherwise pull it up into the rectum whereby it will not perform its sealing function.

Hence, there exists a need for stabilizing the tube and balloon in place by pulling it down against the interior of the anal opening to maintain the seal between the balloon and the walls of the anus while concurrently preventing involuntary expulsion of the entire tube and balloon.

SUMMARY OF THE INVENTION

It is a purpose of the present invention to provide a new device and method for solving the problem of stabilizing a tube with a balloon thereon in place within a person's anal opening during procedures wherein a liquid is introduced into a person's colon through the anal opening and/or retained therein.

In accordance with the device and method of the present invention, this problem is solved by an arrangement whereby the person's buttocks are squeezed together to apply a significantly greater area of the person's body against the surface of the tube to better hold it in place. Additionally, prior to squeezing together of the person's buttocks, the tube (with the balloon already inflated within the anal opening) may be pulled outwardly to pull the balloon against the interior of the anal opening and stabilized in that position by wrapping a thick cord of absorbent material around the tube up against the outside of the anal opening prior to squeezing together of the bottocks.

The device of the present invention comprises an elongated band formed with strap like ends having connecting means at the outer ends thereof. The band is wrapped around a person after the tube has been placed within the person's anal opening. The central section of the band is placed against the person's abdomen and the outer ends of the band, formed as straps, are made to overlap each other in the area of the person's buttocks and are pulled tight, the straps being so shaped that when they are pulled tight they squeeze the person's buttocks together and in the pulled tight condition they are secured. Each band will have a plurality of straps at its ends and the straps will be so connected that the tube can easily pass through the device between adjacent straps.

Preferred features of the device in accordance with the present invention include utilizing Velcro connecting means and providing a quick release connection at the front of the band, i.e. at the central section thereof, so that when the time comes for removal of the band, it can be removed quickly by this quick release connection without the need for disconnecting the strap ends.

The device may be formed of any convenient material such as a non-woven paper, cloth, plastics, netted material, etc. the straps can be very wide or very narrow; and while there is no specific limitation on the number of straps extending to each side, preferably two or three straps will be provided extending from each side.

In accordance with the method of the present invention for securely holding a tube within a person's anal opening, the tube is first inserted and the balloon expanded in the usual way. If desired, the absorbent cord may be wrapped around the tube at this time to stabilize the balloon at the interior bottom of the anus. Whether or not the cord is used, the buttocks squeezing device of the present invention is then applied by placing the central section against the person's abdomen and pulling the strap ends across the person's buttocks, squeezing the buttocks together and then attaching the strap ends securely in place.

Hence, it is an object of the present invention to provide a new and improved device for squeezing a patient's buttocks together for holding a tube in place within the patient's anal opening.

It is another object of the present invention to provide a new and improved method for holding a tube in place within a person's anal opening.

It is still another object of this invention to provide a new and improved device for squeezing a patient's buttocks together comprising a band placed against a person's abdomen after which the outer ends of the band are pulled tight across the person's buttocks to squeeze them together, said ends, which are formed as straps, then tightly secured in that position.

These and other objects of the present invention will become apparent from the detailed description to follow.

BRIEF DESCRIPTION OF THE DRAWINGS

There follows a detailed description of preferred embodiments of the invention to be read together with the accompanying drawings wherein:

FIG. 6 illustrates another embodiment of a buttocks squeezing device laid out flat.

FIG. 7 illustrates the device of FIG. 6 on a patient, seen from the rear.

FIG. 8 illustrates the device of FIG. 6 on a patient and viewed from the left side.

DETAILED DESCRIPTION OF THE PREFERRED EMBODIMENTS

Figure 1:
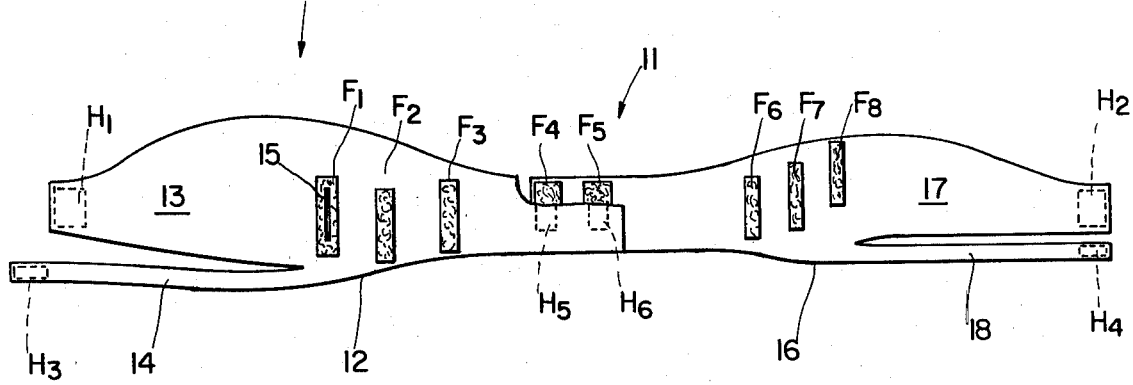
FIG. 1 illustrates the exterior of a buttocks squeezing device of the present invention laid out flat, prior to use.

Referring now to the drawings, like elements are represented by like numerals throughout the several views.

Figure 5:
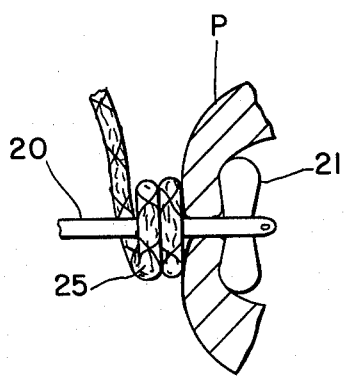
FIG. 5 is a cross-sectional view of a person's anal opening with a tube and balloon in place and with the cord of FIG. 4 wrapped around the tube.

Although the device and method of the present invention may have many different uses, a primary use is to retain in place within a person's anal opening a tube which has been introduced therein for purposes of introducing a liquid into the colon. Such a tube which is designated as 20 is shown in FIG. 5 with an opening at the end thereof and with a balloon 21 also attached to the end thereof, said balloon having been inflated after the tube and balloon have entered the rectum.

While it is always advantageous to be sure that the tube is held in place as desired during any given procedure, the present device and method are particularly suitable with the method and technique as set forth in my above noted prior application wherein there is introduced into the colon a much larger volume of liquid than has been used in cleansing procedures heretofore, namely enough liquid to completely fill the colon and distend the walls thereof. Moreover, this increased volume of liquid is held within the colon for a short period of time before the tube is removed, permitting the person to expel the contents of the colon.

Figure 2:
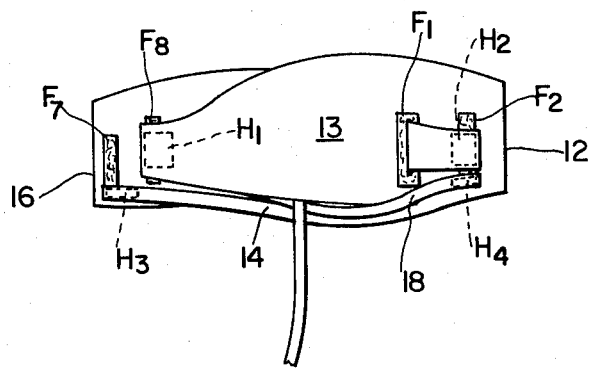
FIG. 2 illustrates the device of FIG. 1 as it would appear from the back when in place and attached on a user.
Figure 3:
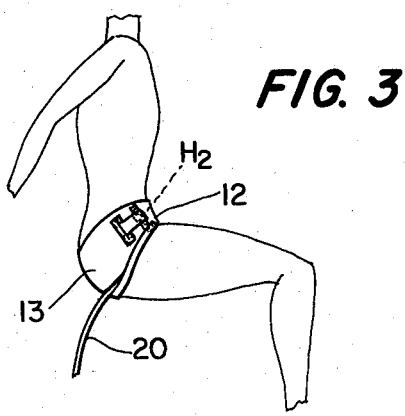
FIG. 3 is a schematic view from the side of a person wearing the buttocks squeezing device of FIGS. 1 and 2.

A preferred embodiment of the invention is illustrated in FIGS. 1-3. The device may be made of any suitable material having sufficient strength. In a preferred form of the invention, the device is made of a non-woven cotton paper material while in other embodiments it may be made of cloth, plastic, a netted material, etc.

Referring to FIGS. 1 through 3, the buttocks squeezing device 10 has a central section 11 which will be placed against the front of the person, i.e. against the abdomen. Specifically, FIG. 1 illustrates the exterior of the device, meaning the surface which will face the exterior after the device has been wrapped around the wearer.

The device is in the form of a band. For reference purposes, the part to the left in FIG. 1, represented by the numeral 12, will be referred to hereinafter as the "right part" because it will be wrapped around the right side of the wearer while the part toward the right hand side in FIG. 1, referred to by the numeral 16, will be referred to hereinafter as the "left part" because it will be wrapped around the left side of the wearer.

Right part 12 is formed at its outer extremity with a pair of straps 13 and 14 while left part 16 is formed at its outer periphery as a pair of straps 17 and 18. In this embodiment the upper straps 13 and 17 are formed as large main straps while the lower straps 14 and 18 are rather narrow. This arrangement has the advantage of efficiency and simplicity, i.e. it involves a small number of straps, and yet they are sufficient to carry out the purpose of the present invention.

Although certain features illustrated in FIG. 1 will be more readily understood in the subsequent description of the operation of the device, it is nonetheless helpful to specifically identify all elements of the band at this point. When the band is applied the various parts will preferably be connected together by Velcro connections. As is well known, Velcro comprises the engagement of a pad having small hooks thereon, referred to hereinafter as "hook pads" with other pads formed of a felt material and referred to hereinafter as "felt pads." In FIG. 1 each of the felt pads are referred to by the capital letter "F" followed by a subscript to specifically identify that pad, especially in the subsequent views. Similarly, all of the hook pads are identified by the capital letter "H" followed by a subscript so that any specific hook pad can also be identified in the subsequent views. In FIG. 1 all of the felt pads face the viewer and are hence shown in solid lines (except for a portion of F4 which is hidden as will be explained below). All of the hook pads are hidden in FIG. 1, i.e. on the opposite side of the band as shown therein, and hence they are shown in dotted lines in FIG. 1.

Finally, in FIG. 1 there is also shown a slit 15 which passes completely through the device and in a manner which will be described in greater detail below, is adapted to receive the outer end of strap 17 when the band is applied to the person.

Figure 4:
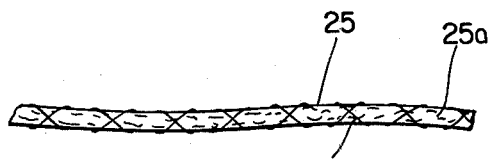
FIG. 4 illustrates a section of an absorbent cord which could be used in accordance with the present invention.

FIG. 4 illustrates a type of cord which can be wrapped around the tube 20 to stabilize the balloon 21 in place. This cord is characterized by a wide body of absorbent material 25a such as cotton or the like formed as elongated strands and held together by threads 25b. After the tube 20 has been inserted into the person's anal opening and the balloon 21 expanded, the tube is pulled outwardly to pull the balloon 21 against the inside of the anal opening and the absorbent cord 25 can then be wrapped around the tube 20. The absorbent characteristics of this cord tend to absorb liquid and hence create a frictional engagement between the cord, the tube and the outer surface of the person's anal opening. It will be understood that the use of this cord 25 is optional and that the use of the buttocks squeezing device to be described below does not necessitate prior use of such a cord.

Referring once again to FIGS. 1-3, initially the device is formed as one elongated band. The central section includes a quick release mechanism formed by making the band of two parts, one having felt pads F4 and F5 and the other having hook pads H5 and H6. Actually, if a quick release mechanism is not formed, the whole band can be formed of a single piece, eliminating F4, F5, H5 and H6. But if it is formed in this preferable manner with this quick release mechanism, it will be understood that initially H5 and H6 are connected to H4 and H5, i.e. this quick release mechanism has no function until it is subsequently desired to remove the band from the wearer.

In the use of the device and in the method of the present invention, after the tube 20 has been inserted and the balloon 21 inflated, with or without use of the cord 25, the device 11 is placed against the wearer with the central section 11 against the wearer's abdomen. The strap ends are then pulled across the person's buttocks with the outer end of strap 17 passing through the slit 15. These straps are then pulled tight and secured in position with hook pad H2 secured to any one or more of felt pads F1, F2 or F3 and with the hook pad H1 at the end of strap 13 connected to any one or more of felt pads F6, F7 or F8. It will be noted that felt pads F1-F3 and F6-F8 have a greater height than the height of hook pads H1 or H2. The reason for this is to provide some room at the bottom of felt pads F1-F3 and F6-F8 for having secured thereto hook pad H4 on strap 18 and H3 on strap 14, respectively. In applying the device, after the hook pads H1 and H2 have been secured in place, the straps 14 and 18 are in fact pulled tight and connected to said felt pads.

FIG. 2 illustrates the back of the device as it would appear secured in place on a person.

The reason for having a plurality of straps at each end is to squeeze the buttocks together on both sides, i.e. above and below the tube. Hence, in FIG. 2 the tube 20 would pass through the device below the straps 13 and 17 and above the straps 14 and 18.

FIG. 3 illustrates the device of FIGS. 1, 2, applied to a wearer and viewed from the wearer's right side.

FIGS. 6 through 8 illustrate another embodiment of the present invention. As shown therein the band 60 has a right side 62 and a left side 63. As with FIG. 1, FIG. 6 views the outer side of the device, i.e. the side which would face away from the wearer when the band is in use. The left and right sides join along a central section which, like the embodiment of FIG. 1, is narrower than the remainder of the device so as not to inhibit the person's bending his legs at the hips. While this embodiment illustrates a quick release device, it will be understood that it can also have a solid central section if so desired. It will be understood that in the present embodiment as well as the embodiment of FIGS. 1-3, however, this quick release means may take any other form such as buckles, snaps, etc.

The device of FIGS. 6-8 includes a plurality of straps 67, 69 and 71 on the right side, each having at its outer end a felt pad 68, 70 and 72, respectively (these pads are on the opposite side and hence not visible in FIG. 6). Between the planes of these straps there are provided Velcro hook pads 64, 65 and 66. On the left side there are provided further series of straps 75, 77 and 79, each with a similar felt pad 76, 78 and 80, respectively. While the pad 78 is not visible, the pads 76 and 80 are visible since the ends of straps 75 and 79 have been turned back. Also included are Velcro hook pads 72, 73 and 74 located between the planes of the straps 75, 77 and 79. It will be observed that the three straps on each side are spaced vertically from the planes of the three straps on the other side, and each of the six straps in fact lines up horizontally with a Velcro hook type pad on the opposite side. In operation of the device 60, the tube 20 with balloon 21 would first be inserted. Referring to FIG. 7, the attendant would then apply device 60 by wrapping the device 60 around the patient, at first with none of the straps attached but with 62a and 63a secured together. To squeeze the buttocks together it is preferable to start from the bottom and work up. The operator would grab the two straps 71 and 79 and pull them tightly to the left and right, respectively, attaching the strap 71 by connecting the felt pad 72 to the Velcro hook pad 74. The operator would then grab the two straps 79 and 69 and pull them to the right and left, respectively, attaching the pad 80 to the Velcro hook pad 66. This process would be repeated until all of the straps were attached in this manner.

While Velcro attachments are preferable in both of the illustrated embodiments, it will be apparent that other types of attaching means such as belt buckles and the like will also be operable in carrying out the present invention.

Although the invention has been described in considerable detail with respect to preferred embodiments thereof, it will be apparent that the invention is capable of numerous modifications and variations, without departing from the spirit and scope of the invention, as defined in the claims.

I claim:

1. A device for squeezing a person's buttocks together to hold a tube in place in the person's anal opening, comprising:
   an elongated band shaped to wrap around a person's mid-section including the lower abdomen in the front, the hips on the side and the buttocks in the back,
   the central section of the band adapted to fit against the front of the person while the ends of the band are adapted to overlap in the back of the person such that when the device is pulled tight and secured, the band pulls the person's buttocks together,
   each said end of the band formed as a plurality of straps, each said strap including a first connecting means at the outer end thereof, said band further including, on both sides of said central section, second connecting means positioned to cooperate with the first connecting means of the end of the strap farthest therefrom to form a connection therewith,
   whereby with the band wrapped around the person, generally opposed straps are pulled to tighten the band on the person and then its first connecting means is connected to its corresponding second connecting means to tighten the band and hold the person's buttocks together.

2. A device according to claim 1, said connecting means being Velcro of the type having a hook pad to felt pad connection, with one of the first or second connecting means being the felt pad of the Velcro, and the other being the hook pad thereof.

3. A device according to claim 2, said device being made of a non-woven cotton paper material.

4. A device according to claim 2, said band ends including large upper straps which overlap each other with one passing through an opening in the other and thinner lower straps.

5. A device according to claim 4, wherein the first connecting means are hook pads and the second connecting means are felt pads.

6. A device according to any one of claims 1-5, wherein the central section of the band includes a quick release connection.

7. A device according to claim 6, wherein the quick release connection is Velcro.

8. A device according to claim 1, each second connecting means being provided on the end of the band between the straps, one such second connecting means positioned opposite each strap for cooperating with the first connecting means on that strap.

9. A device according to claim 8, the straps and second connecting means at each end of the band alternating with each other along that end, and the straps at one end being staggered relative to the straps at the other end, whereby in applying the device to a person, the straps may be alternatively tightened and connected, in sequence, first from one side and then from the other side.

10. A device according to claim 8, wherein the connecting means are Velcro.

11. A device according to claim 10, wherein the tube passes between the straps.

12. A device according to claim 11, wherein the straps are close enough to each adjacent strap such that the tube passing between the straps is virtually engaged by adjacent straps.

13. A device according to claim 8, wherein the band is substantially narrower in the central section located against the person's lower abdomen, whereby in use the narrow front portion permits the person to bend at the hips.

14. A device according to claim 8, wherein the band further includes at the central section thereof a quick release connection permitting quick removal of the device from the person without having to disconnect the straps from each other.

15. A device according to claim 14, said quick release connection being a Velcro connection.

16. A method for holding a tube securely in a person's anal opening comprising the steps of:
inserting into a person's anal opening a tube having a balloon near the end thereof and then inflating the balloon when it is inside the person's anal opening to position it therein,
and preventing removal of the balloon by pushing the person's buttocks together, said pushing including; wrapping a band around the person's mid-section including the abdomen, the hips and the buttocks by placing the central section of the device against the person's abdomen and pulling the ends thereof tight as the ends overlap at the person's buttocks to pull the person's buttocks together to hold the tube tightly in place.

17. A method according to claim 16, wherein the step of pulling the ends of the band include pulling a plurality of straps from each end of the band, at least one strap located above the tube and at least one strap located below the tube so that the tube passes between the straps.

18. A method according to claim 16 or claim 17, including the step of wrapping a thick cord of absorbent material around the tube up against the anal opening before applying the band.

* * * * *